United States Patent [19]

Ferrari

[11] Patent Number: 5,387,521
[45] Date of Patent: Feb. 7, 1995

[54] GENE EXPRESSION IN BACILLI

[75] Inventor: Eugenio Ferrari, San Bruno, Calif.

[73] Assignee: Genencor International, Inc., Rochester, N.Y.

[21] Appl. No.: 71,210

[22] Filed: Jun. 2, 1993

Related U.S. Application Data

[63] Continuation of Ser. No. 692,108, Apr. 26, 1991, abandoned.

[51] Int. Cl.⁶ .......................... C12N 1/21; C12N 9/00; C12N 9/42; C12N 9/54
[52] U.S. Cl. ................. 435/252.31; 435/183; 435/198; 435/209; 435/221
[58] Field of Search ............ 435/252.31, 221, 69.1, 435/172.3, 183, 198, 209

[56] References Cited

U.S. PATENT DOCUMENTS 4,801,541  1/1989  Yoneda et al. ................. 435/172.3

OTHER PUBLICATIONS

Yoneda, "Increased Production of Extracellular Enzymes by the Synergistic Effect of Genes Introduced Into *Bacillus subtilis* by Step-Wise Transformation," Applied and Environmental Microbiology 39(1):277-279, (Jan. 1980).

Henner et al., "Location of the Targets of the hpr-97, SacU 32(Hy) and SacQ36(Hy) Mutations in the Upstream Regions of the Subtilisin Promoter," J. of Bacteriology 170(1):296-300 (Jan. 1988).

*Primary Examiner*—Richard A. Schwartz
*Assistant Examiner*—Philip W. Carter
*Attorney, Agent, or Firm*—Margaret A. Horn

[57] ABSTRACT

The invention relates to genes, vectors and Bacilli transformed with them which are useful in the hyperproduction of enzymes. The invention also relates to processes for producing enzymes using the genes, vectors and organisms of the invention.

5 Claims, 3 Drawing Sheets

GENE EXPRESSION IN BACILLI

This is a continuation of application Ser. No. 692,108 filed Apr. 26, 1991, now abandoned.

FIELD OF THE INVENTION

The invention relates to novel genes, vectors and Bacilli transformed with them useful in the hyperproduction of enzymes. Specifically, the invention relates to specific combinations of unlinked genes which, either mutated or wild type, synergistically induce hyperproduction of enzymes.

BACKGROUND OF THE INVENTION

Many industrially important products are produced from members of the genus Bacilli. Some of these include proteases, amylases, and beta-glucanases (Priest, 1977, Bacteriological Review, 41: 711–753). Most of these enzymes are either produced by Bacilli after the initiation of sporulation or are timed with the onset of the stationary phase.

*Bacillus subtilis* I-168 is the most extensively studied member of the Bacilli and has a well developed genetic system as the result of many years of academic research. As a result, there is a considerable amount of knowledge pertaining to the expression of extracellular enzymes and many mutants of *B. subtilis* I-168 exist that are altered in the expression of these enzymes. There are several different known genes which code for proteins that regulate the expression of extracellular enzymes. Although the exact molecular mechanism of this regulation is not completely understood, it is now clear that the product of these genes interact either directly or indirectly at the transcriptional level of the target enzymes (Ferrari et al, 1988, J. Bacteriol. 170: 289–295; Henner et al, 1988, J. Bacteriol. 170: 296–300).

Regions of the DNA around promoters can actively interact with certain transcriptional control factors and effectively regulate the strength and efficiency of a particular promoter. This interaction will result either in a stimulation or in a repression of the transcription of that particular target gene. As a consequence, mutations in either the genes coding for these transcriptional control factors or in regions of the chromosome with which they interact are expected to yield more or less mRNA of the target gene. This in turn will result in higher or lower amounts of enzyme synthesized by the cell.

With the advent of genetic engineering techniques, it has been possible to clone and express a gene from another species in *B. subtilis* I-168 or other Bacillus species. Most of these studies have involved the use of multicopy plasmids as cloning vectors. Although the yield of the cloned protein was increased significantly over the production in the wild type host, it was far below the yield of enzyme reported for production strains obtained through mutagenesis. This was also the case when the enzyme was under the control of strong transcriptional and translational elements derived from *B. subtilis*. Apparently the production of enzyme obtained from the multicopy, replicating plasmids was not affected by the presence of certain mutations, i.e. sacU(Hy), sacQ(Hy) and hpr (Dedonder et al, Microbiology 1976, D. Schlessinger (Ed), pp 58–69, American Society for Microbiology, Washington, DC; Palva et al. 1983, FEMS Microbiology Letters, 17: 81–85; Ferrari, unpublished observation), described as being able to induce hyperproduction of several secreted enzymes. These regulatory genes are unlinked to the structural gene for the affected enzymes and therefore one should expect that they exert their stimulating activity to a greater degree also when the gene is present in a multicopy plasmid.

There are at least 6 different regulatory genes known to interact either directly or indirectly with the transcription of the subtilisin gene: sacU, sacQ, prtR, hpr, sin and abrB.

Certain mutations in the sacU gene encode for a modified polypeptide which has the most pleiotropic effect among all these known regulatory genes. A strain carrying for example sacU (Hy) mutations can sporulate in presence of high levels of glucose, has a very low efficiency of transformation, lacks flagella and it is also responsible for the hyperproduction of several secreted enzymes. (Dedonder et al, Microbiology 1976, see above).

The sacQ gene from three different bacilli has been cloned and characterized (Amory et al, 1987, J. Bacteriol, 169, 234; Yang et al, 1986, J. Bacteriol, 166, 133; and Tomioka et al, 1985, J. Biotechnol 3,85). The gene isolated from *B. subtilis* encodes a 46 amino acid polypeptide. The sacQ gene when hyperexpressed either because of a mutation in its promoter or when present in a multicopy plasmid causes hyper production of certain extracellular enzymes, including the alkaline protease (Yang et al, 1986, J. Bacteriol 166, 113–119).

The prtR gene encodes a 60 amino acid polypeptide. When this gene is present in *B. subtilis* in a multicopy plasmid it causes increased production of proteins. However, unlike for sacQ, there have been no chromosomal mutations to date for this gene which increases protease production (Yang et al., 1987, J. Bacteriol. 169, 434–437).

The hpr gene encodes a 203 amino acid protein and certain mutations in this gene stimulate alkaline protease production. It has been established that mutations which cause the loss of this gene product stimulate transcription of the subtilisin gene (Perego and Hoch, 1988, J. Bacteriol. 170, 2560–2567). The product of the hpr gene therefore is most likely a repressor of the subtilisin gene. It has also been determined that the scoC gene and possibly the catA gene are identical to the hpr. The notation hpr will be used thereafter to refer to any of the three alleles called hpr, scoC or catA.

The sin gene encodes a polypeptide of 111 amino acids (Gaur et al, 1986, J. Bacteriol, 168: 860–869). An insertional inactivation of the gene causes the production of a higher level of alkaline protease, suggesting that this gene also acts as a repressor of the expression of alkaline protease.

Finally the abrB gene codes for a polypeptide of 97 amino acids. Also for this gene there is evidence that it is a repressor of the transcription of the alkaline protease and might have an important role in the temporal regulation of this gene.

SUMMARY OF THE INVENTION

It has been surprisingly discovered that a synergistic effect can be achieved in a strain carrying combinations of mutations in these genes. Such organism when transformed with an integrative vector or plasmid in which the enzyme to be expressed is under the control of the promoter with all its regulatory regions, will express more enzyme than predictable from using either a replicative multicopy plasmid or only one of the above described regulatory mutated genes.

Accordingly, the invention relates to a Bacillus able to hyperproduce an enzyme comprising:
a) the enzyme gene sequence;
b) a functional promoter gene sequence controlling the expression of the enzyme gene operably linked to the enzyme gene sequence; and
c) two or more mutated genes involved in the transcriptional regulation of the promoter wherein each individual mutated gene induces the increased production of the enzyme. The mutated genes are preferably selected from the group comprising: hpr, sacQ, sacU sin, abrB, or prt R The invention also relates to vectors comprising the novel gene, to cells transformed with the vectors and to a process for making enzymes.

DETAILED DESCRIPTION

Figure 1:
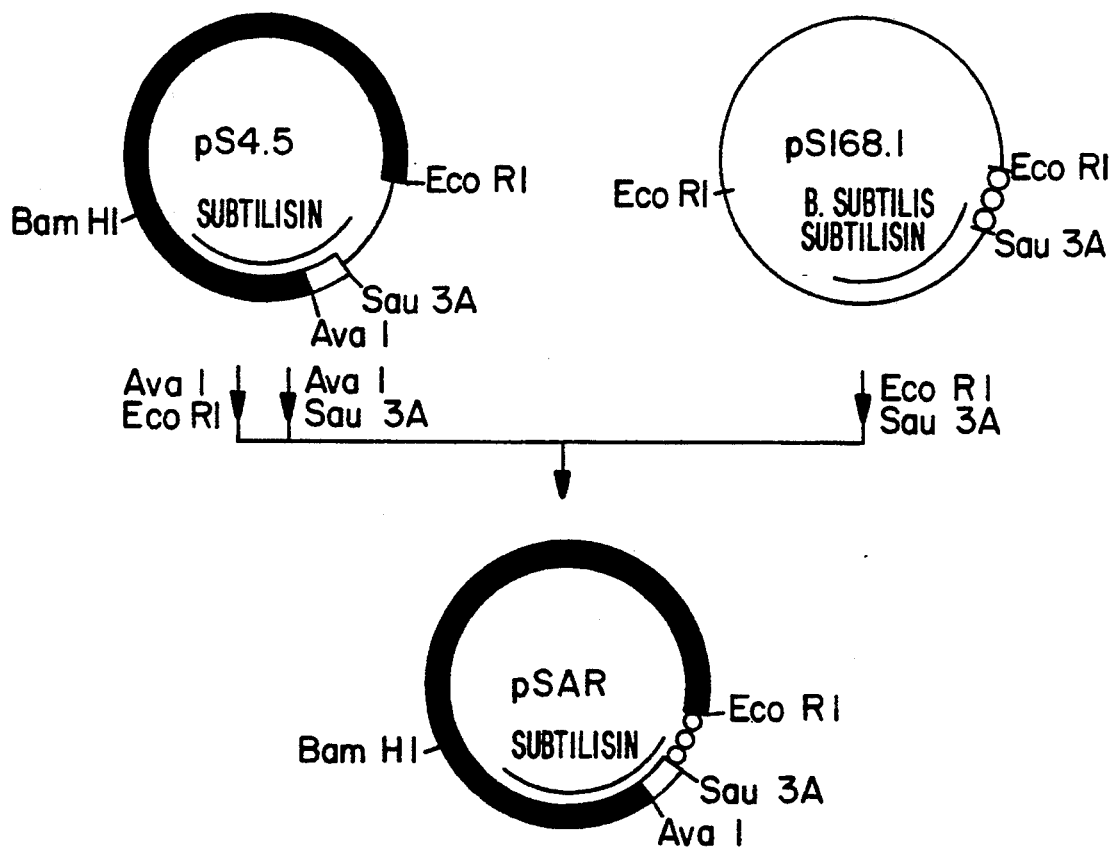
FIG. 1 shows the construction of the pSAR gene.

Applicants have demonstrated novel combinations of mutated or wild type genes, vectors and Bacilli transformed with them which are unique in their ability to induce hyperproduction of enzymes. Two mutated genes as described above are introduced in a strain carrying an appropriate promoter and gene sequence. The promoter sequence and the gene sequence of the enzyme are introduced into such host strain by means of an integrative vector. Such vector, which may or may not be amplified upon integration, is stably maintained as part of the host genome and replicates within the cell as an integral part of its chromosome. Integration can occur at different regions of the chromosome including but not limited to the region of homology with the promoter used in a particular construction. Such host may have its original enzyme sequences, or other gene sequences, deleterious to the desired enzyme production, deleted or otherwise made inoperative by standard techniques.

As used herein, the "enzyme gene-sequence" or enzyme structural gene refers to a DNA sequence encoding for the expression of an enzyme, in general either heterologous or homologous to Bacilli. Several enzymes are known and within the scope of this teaching including but not limited to those preferred enzymes from *Bacillus lentus, Bacillus amyloliquefaciens* (e.g., ATCC 23844), *Bacillus licheniformis* (e.g., ATCC 21415), *Bacillus alcalophilus* (e.g., ATCC 21522), *B. subtilis* (e.g., ATCC 6051) and *Bacillus cereus* (e.g., ATCC 21768). Also included are all the genes capable of being expressed in Bacillus such as the ones coding for proteases, lipases, cutinases, esterases, endoglycosidases, etc. A preferred enzyme is subtilisin. Other preferred enzymes include endoglycosidase H from Streptomyces species and lipase from *Pseudomonas mendocino* ATCC 53552 (available from American Type Culture Collection, Rockville, Md.). Enzymes such as subtilisin which act at an optimum at higher pH are among the preferred enzymes. It is also recognized that only those promoters which are affected (i.e. hyperproduce) by each of the transcriptional regulatory genes alone are intended to be covered by the invention (e.g. aprE and nprE). The enzyme gene sequence also includes the DNA sequence encoding for a naturally occurring enzyme gene sequence which is modified to produce a mutant DNA sequence which encodes a substitution, insertion or deletion of one or more amino acids in the gene sequence. Suitable modification methods are disclosed in, for example, EPO Publication No. 0130756, published Jan. 9, 1985. The enzyme gene may be fused to at least a portion of a second gene.

Subtilisins are bacterial alkaline proteases which generally act to cleave peptide bonds of proteins or peptides. As used herein, "subtilisin" means a naturally occurring subtilisin or a recombinant subtilisin. A series of naturally occurring subtilisins is known to be produced and often secreted by various bacterial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases beth have a catalytic triad comprising aspartate, histidine and serine. In the subtilisin related proteases the relative order of these amino acids, reading from the amino to carboxyl terminus is aspartate-histidine-serine. In the chymotrypsin related proteases the relative order, however, is histidine-aspartate-serine. Thus, subtilisin herein refers to a serine protease.

"Recombinant subtilisin" refers to a subtilisin in which the DNA sequence encoding the subtilisin is modified to produce a mutant DNA sequence which encodes the substitution, deletion or insertion of one or more amino acids in the naturally occurring subtilisin amino acid sequence. Suitable methods to produce such modification include those disclosed herein and in EPO Publication No. 0130756. For example, a subtilisin multiple mutant containing the substitution of methionine at amino acid residues 50, 124 and 222 with phenylalanine, isoleucine and glutamine, respectively, can be considered to be derived from the recombinant subtilisin containing the substitution of glutamine at residue 222 (Gln-222) disclosed in EPO Publication No. 0130756. The multiple mutant thus is produced by the substitution of phenylalanine for methionine at residue 50 and isoleucine for methionine at residue 124 in the Gln-222 recombinant subtilisin.

As used herein, "a functional promoter sequence controlling the expression of the enzyme gene operably linked to the enzyme gene sequence" refers to a promoter sequence which controls the transcription and translation of the coding sequence in Bacillus. The promoter sequence is chosen so that it is functional in the microorganism chosen for expression. For example, promoter sequence (including ribosomal binding sites) formed from Lambda P (Renaut, et al., Gene 15, 81 [1981]) as well as the trp (Russell, et al., Gene 20, 23 [1982] or tac (de Boer et al., PNAS. USA 80, 21 [1983]) may be operably linked to coding sequences to express alkaline protease in *E. Coli*. When *B. subtilis* I-168 is the expression host, the *B. subtilis* alkaline protease promoter (Stahl et al, J. Bacteriol 158, 411–418 [1984]) alpha amylase promoter of *B. subtilis* (Yang et al., 1983, Nucleic Acids Res. 11, 237–249) or *B. amyloliquefaciens* (Tarkinen, et al, J. Biol. Chem. 258, 1007–1013 [1983]), the neutral protease promoter from *B. subtilis* (Yang et al, J. Bacteriol, 160, 15–21 [1984]) or any other promoter from *B. subtilis* or other related Bacilli, whose expression is affected by the described upstream regulatory genes may be used. The preferred promoter of the invention is the aprE promoter. Also preferred is the nprE promoter.

As used herein, "transcriptional regulatory genes" refers to any of the genes whose product affects the level of transcription from the enzyme promoter. These gene products can interact at the promoter level (e.g. AbrB) or with a region upstream or downstream of it (e.g. Hpr, SacU, SaoQ, PrtR, Sin) either directly or indirectly. The definition above is comprehensive of the gene product or the lack of it and any possible mutation which may increase the level of transcription of a particular promoter (e.g. multiple copies). This definition is meant to include but not limited to certain rotations in the promoter region, downstream or upstream of the promoter region of the target gene which may result in an increase in transcription due to a better interaction or lack of it with the regulatory genes or with the transcriptional machinery (e.g. RNA polymerase, mutations which decrease production of a gene product which interferes with transcription). These genes and the effect of their mutations are described above. These specific combinations, applicant has discovered, exhibit a synergistic effect when compared with the results predicted from either single mutations alone.

It appears that in order to express the enzyme at high levels and have its expression more effectively under the control of these regulatory mutations the promoter needs to be integrated into the genome of the host Bacillus cell or perhaps be carried by a low copy number plasmid. High copy number replicating plasmids carrying the enzyme gene seem to be poorly tolerated in strains bearing some of the regulatory mutations, and they are lost or rearranged at very high frequency.

It is preferred that the gene coding for the enzyme to be expressed at high levels is integrated into the genome of the host Bacillus cell.

"Expression vector" refers to a DNA construct containing a DNA sequence which is operably linked to a suitable control sequence capable of effecting the expression of the DNA in a suitable host. Such control sequences can include a promoter to effect transcription or optional operation sequence to control such transcription, a sequence encoding a suitable ribosome binding sites (RBS) and sequences which control termination of transcription and translation. The vector may be a plasmid, a phage particle, or a potential genomic insert. Once transformed into a suitable host, the vector may replicate and function independently of the host gene or may integrate into the gene itself. A preferred vector is pSAI.

Bacillus host cells for the purpose of this invention are those Bacillus hosts capable of functionally accepting the expression vector. Preferably, they have been manipulated by the methods disclosed in EPO Publication No. 0130756 to render them incapable of secreting other enzymes deleterious to the desired enzyme. A preferred host cell for expressing subtilisin is the *B. subtilis* strain BG 2036 which is deficient in enzymatically active neutral protease and alkaline protease (native subtilisin). The construction of strain BG 2036 is described in detail in EPO Publication No. 0130756 and further described by Yang, et al (1984) J. Bacteriol. 160 15-21. Other host cells for expressing subtilisin include any derivative of *B. subtilis* I-168 and any other member of the bacillus family in which such system might work (i.e. *B. amyloliquefaciens* and *B. licheniformis* (EPO Publication No. 0130756).

"Operably linked" as used herein describes the relationship between two DNA regions and means they are functionally related to one another. For example, a promoter is operably linked to the gene sequence coding for an alkaline protease if it properly controls the transcription of the sequence.

The following examples are not intended to be limiting. One skilled in the art could choose other promoters, find or use other mutations and express other enzymes in Bacillus. Also, one can easily see that one skilled in the art could replicate the teachings of examples with materials generally available to the public. Accordingly, none of the strains herein need be deposited.

DESCRIPTION OF THE PREFERRED EMBODIMENTS

Cloning of the Subtilisin Gene

The subtilisin gene from *B. amyloliquefaciens* was isolated as described by Wells et al, 1983, *Nucleic Acid Res.* 11: 7911-7925. Briefly, partially Sau3A digested chromosomal DNA from *B. amyloliquefaciens* was ligated to BamHl digested pBS42 and used to transform *E. coli*. pBS42 is a plasmid vector composed of an origin of replication from pUB110 recognized as such by *B. subtilis*, an origin of replication from pER322 which allows replication of the plasmid in *E. coli* and a chloramphenicol acetyltransferase (CAT or CmR) from pC194, a fully characterized plasmid from *Staphylococcus aureus* (Horinouchi and Weisblum, 1982), which can express CmR in both *E. coli* and *B. subtilis*. Synthetic DNA probes designed from the known amino acid sequence of the subtilisin were used to isolate a plasmid (p54) carrying the DNA coding for the gene. The isolated DNA fragment was able to code for subtilisin production when transferred to *B. subtilis* and the DNA sequence translated to match the published amino acid sequence of the alkaline protease (Wells et al, 983, *Nucleic Acid Res.* 11: 7911-7925).

A Sau3A BamH1 fragment from pS4-5 (a derivative of pS4) comprising the subtilisin structural gene from the 8th codon of the signal sequence to 250 bp after the 3' end of the gene (all of which is *B. amyloliquefaciens* DNA), was fused to a 750 bp EcoR1-Sau3A fragment which carries the promoter and the first 8 codons of the translated sequence of the *B. subtilis* subtilisin gene (FIG. 1). The gene so reconstructed, carried in an EcoRl-BamHl fragment containing only Bacillus DNA, was inserted in BamHl-EcoRl digested pBS42 resulting in plasmid pSAR. This plasmid was shown to be able to produce subtilisin in *B. subtilis*.

The EcoRl-BamHl fragment from pSAR, carrying the *B. subtilis* aprE promoter fused to the *B. amyloliquefaciens* subtilisin gene was ligated to an EcoRl-BamHl digested pJH101 (Ferrari, et al, *Journal of Bacteriol.* Vol. 154, pp 1513-1515). The resulting plasmid, which can replicate in *Escherichia. coli* but not in *B. subtilis* was called pSA1. Upon transformation in *B. subtilis*, followed by Chloramphenicol selection, this plasmid will integrate into the chromosome at the site of homology with the aprE promoter.

The CmR gene from pC194, contained in a 1.6 Kilobases (Kb) ClaI fragment, was cloned in ClaI digested pBR322. Upon digestion with EcoRl and HindIII, this plasmid will release the CmR resistance gene flanked by a few basepairs of pBR322 origin (see below).

Figure 2:
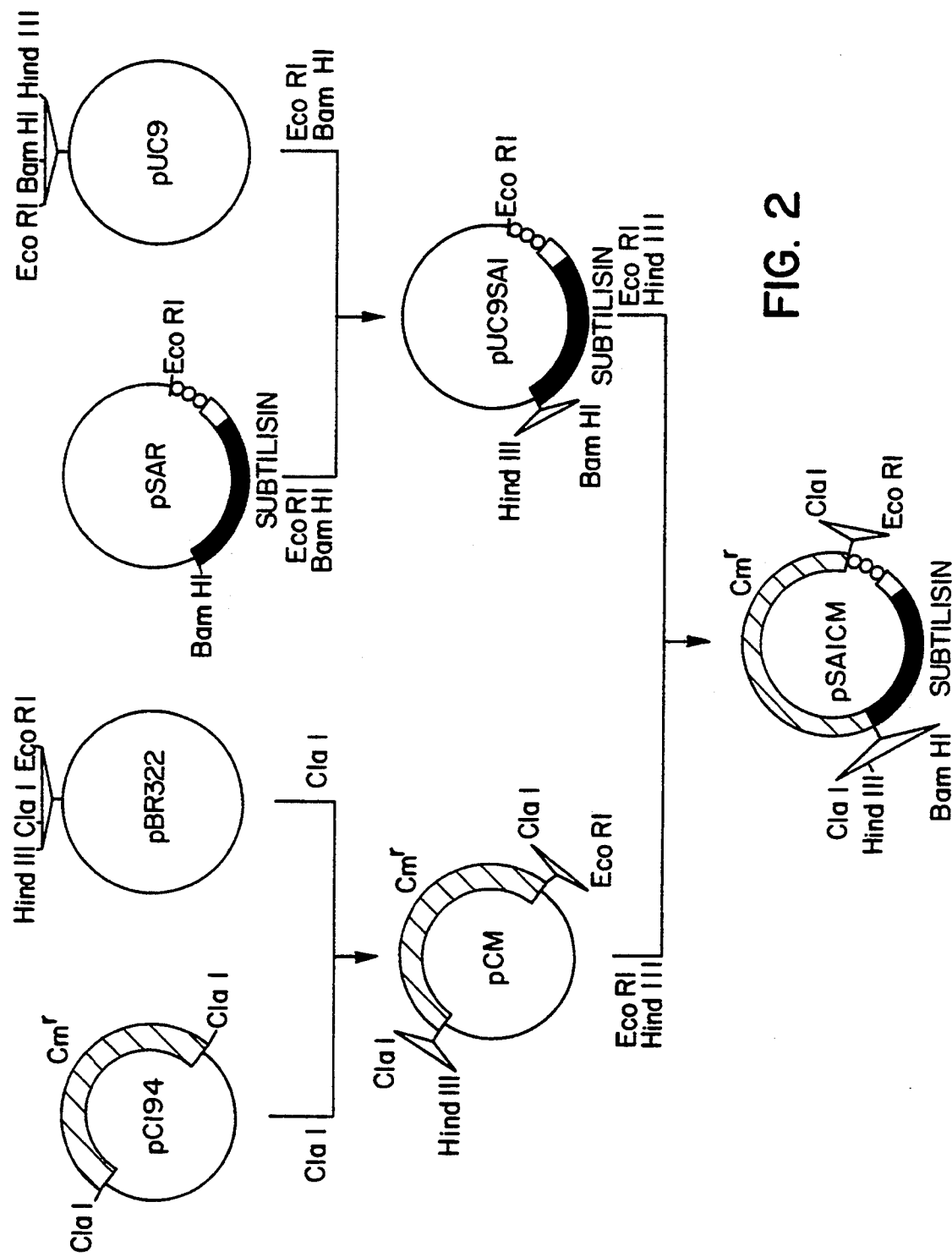
FIG. 2 shows the construction of the pSAICM gene.

The EcoRI-BamHI fragment from either pSAR or pSAI carrying the subtilisin gene was subcloned in the EcoRI-BamHI sites of the synthetic polylinker region of pUC9. Upon digestion with EcoRI and HindIII, this plasmid will release a 2.2 Kb fragment carrying the subtilisin gene flanked on one side by 17 bp of the synthetic linker (FIG. 2).

Figure 3:
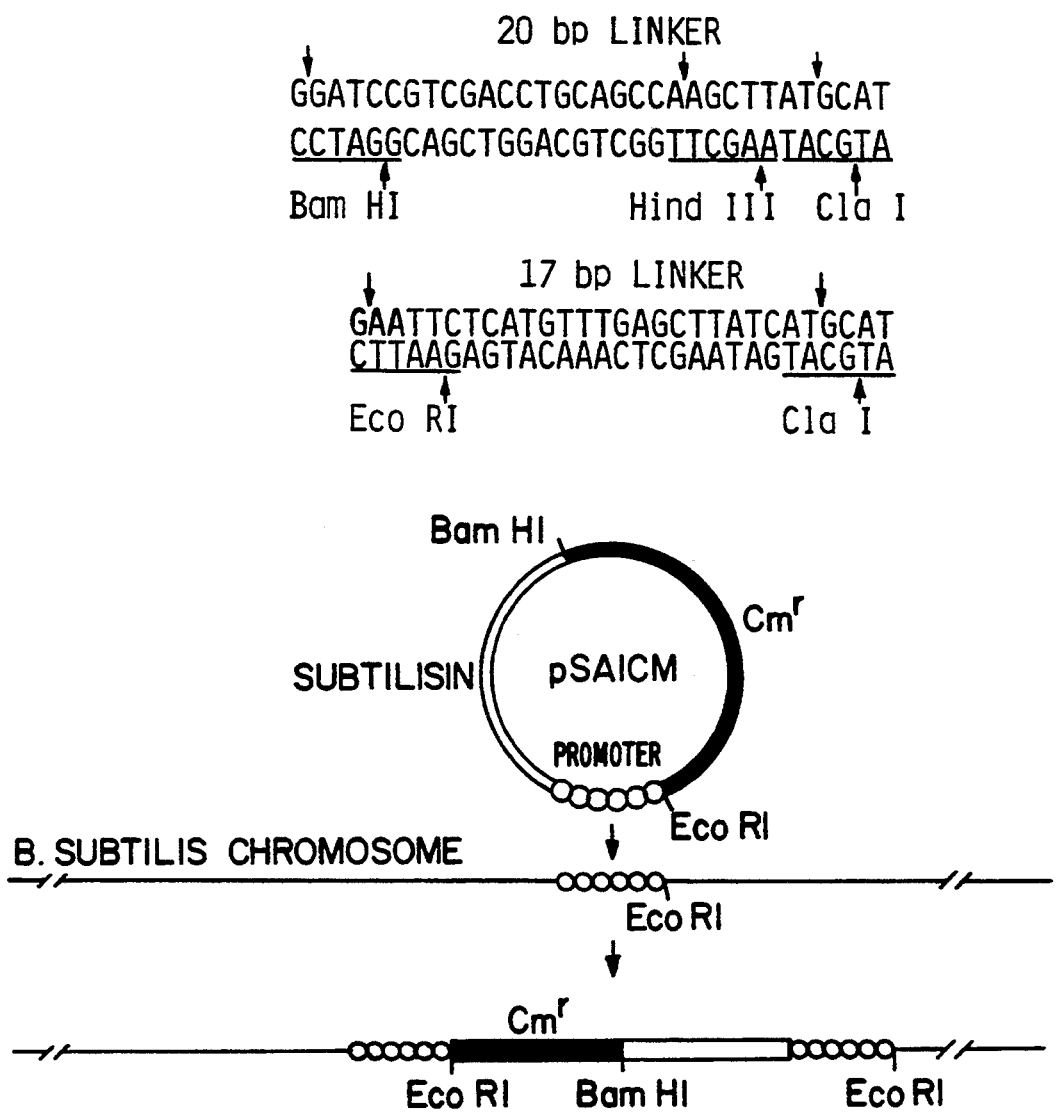
FIG. 3 shows the integration of the pSAICM gene into the B. subtilis chromosome. The 20 bp linker is SEQ ID NO:1 and the 17 bp linker is SEQ ID NO:2.

These two EcoRI-HindIII fragments were ligated together and used to transform B. subtilis, selecting for CmR. Upon transformation this plasmid integrates into the chromosome, as has been shown by PBS1 transduction (FIG. 3). The final construction in B. subtilis consists of 1.6 Kb from pC194 and the subtilisin gene joined together by short linker regions. One linker is composed of 20 bp from pUC9, and the other one consists of the 17 bp from pBR322 included between the EcoRI and the ClaI sites.

In order to obtain a strain which produces mainly the protease we are interested in, we deleted the two major proteases, present in almost all Bacilli (the alkaline protease and the neutral protease), as described by Stahl and Ferrari (1984), J. Bacteriol., 158: 411-418 and Yang et al (1984), J. Bacteriol., 160: 15-21. The plasmid described above was then introduced into BG 2036 by transformation selecting for CmR. This plasmid similarly to pSAI will integrate into the chromosome (we have never been able to detect any replicating plasmids) in the region of homology conferred by the B. subtilis subtilisin promoter (FIG. 3). Southern blot analysis of the chromosomal DNA digested with proper restriction enzymes and PBS1 mapping experiments confirmed the integration and the presence of the proper size fragments.

To obtain hyperproduction we then introduced chromosomal mutations known to increase the level of secreted enzymes, either through competent cell transformation or PBS1 transduction. Both these techniques are commonly used for genetic studies in B. subtilis. The resulting strain is a prototrophic sporeforming derivative of B. subtilis I-168 (catalog No. 1-A1, Bacillus Genetic Stock Center) which carries the B. amyloliquefaciens subtilisin gene and the CmR gene from pC194 integrated into the chromosome.

Construction of Hpr97, ScoC, Cat A Strains

All the strain constructions described here have been carried out by using standard B. subtilis genetic techniques. Transformations have been done following the method described by Anagnostopoulos and Spizizen (J. Bacteriol., 81: 741-746, 1961). Transduction have been done using the bacteriophage PBS1, following the method described by Hoch et al., (J. Bacteriol., 93: 1925-1937, 1967). The integrative plasmid pSAI was introduced into strain BG2097 (a strain publicly available which carries deletions in the aprE and nprE genes) by transformation to generate strain BG3002. DNA prepared from BG3002 was used to transform strains IPCC 7698 (available from the Pasteur Institute Culture Collection, Paris, France), 1A151 (available from the Bacillus Genetic Stock Center, Columbus, Ohio) and Hpr97 (available from Dr J. A. Hoch, Research Institute of Scripps Clinic, La Jolla, Calif.) containing respectively the scoC1, catA or hpr-97 mutation to chloramphenicol resistance. The resulting chloramphenicol resistant strains were scored on solid medium (tryptose blood agar base agar, TBAB) containing skim milk for the detection of the hyperprotease producing characteristic (due to the presence of the scoC, catA and hpr mutations) of the parent strain. PBS-1 lysates (see above) were prepared on the ScoC, CatA and Hpr strains carrying the pSAI integrative plasmid by a standard published technique (Hoch et al 1967, see above). These lysates were used to transduce strain BG2097. These transductions introduced the subtilisin gene integrated in the chromosome with plasmid pSAI into BG2097 and also transferred the scoC or catA or hpr mutations by virtue of their linkage to the aprE gene (that is pSAI). Approximately 10-20% of the chloramphenicol resistant transductants demonstrated a higher amount of protease production, suggesting that these strains had indeed acquired the scoC or catA or hpr hyperproducing phenotype. Some of the transductant were screened on plates containing 1.6% skim milk and compared to BG3002. Transductants able to yield a larger halo on these type of plates were selected and strains BG 3008, BG3005 and BG3007 were obtained. The genotype of these strains is isogeneic (hisA, aprE, nprE, pSAI::CmR) except for the hpr gene were the mutations scoC1, catA or hpr97 are present respectively. When representatives of this transduction were examined in shake flasks using a nutrient broth medium, they produced ~19-17 mg/L subtilisin or 5-10 fold more than the strain that did not contain the hyperproducing mutation.

Construction of SacU(Hy) Strains

One of the properties of SacU(Hy) strains is that they lack the ability to produce flagella and to become motile. Since PBS-1 attaches to motile flagella, it is impossible to prepare a PBS-1 working lysate on SacU(Hy) strains. This problem was circumvented by the isolation of a spontaneous mutant that was motile and retained its protease hyperproducing phenotype. The nature of the mutation that results in motility is unknown. A lysate was prepared on the motile SacU(Hy) strain. This lysate was used to transduce either BG3002 (Δ apr, Δ npr, hisA) containing the pSAI plasmid to histidine prototropy. Since the sacU gene and the hisA gene are linked by transduction, a certain percentage of the transductants were expected to contain the sacU(Hy)32 gene. The presence of this mutation was verified on skim milk plates; ~90% of the transductants exhibited the hyperproducing phenotype. A representative strain containing the sacU(Hy) mutation produced 35-45 mg/L when grown in nutrient broth medium. The same general scheme applied when a strain containing the scoC or catA mutation was transduced with a PBS1 lysate prepared on a SacU(Hy) strain. Strains containing the scoC (BG3008) and catA (BG3005) mutations could be successfully transduced to sacU(Hy). The strains containing both the sacU(Hy)32 and either the scoC or catA mutations exhibited a larger zone of clearing on skim milk plates than did either of the strains containing the individual mutations. These strains produced ~55 mg/L in nutrient broth medium.

Construction of SacQ(Hy) Strains

A lysate was prepared on a SacQ(Hy) strain. This lysate was used to transduce a strain to threonine prototropy. Again, since the thr gene and sacQ(Hy) gene are linked by transduction, a certain percentage of the population would be expected to contain the hyperproducing sacQ(Hy) gene. The same procedure is used to construct strains containing either the sacQ(Hy) mutation alone or in combination with either the scoC or catA mutation.

Construction of Triple Mutants

Strains containing the sacU(Hy)32, sacQ(Hy) and either the scoC or catA mutation could be constructed by using a combination of the above procedures. Generally speaking, the catA/scoC mutation was introduced in one step along with the plasmid pSAI, followed by the introduction of the sacQ(Hy) mutation and finally the sacU(Hy) mutation was introduced into the strain.

Results

| Strain | Enzyme Level Shake Flasks (mg/l) |
| --- | --- |
| BG 3002 (wild type) pSAI | 0.5 |
| BG 3004 sacU(Hy), pSAI | 40 |
| sacU(Hy), pSAI, pBS7AS | 36 |
| BG 3005 catA, pSAI | 2 |
| BG 3006 catA, sacU(Hy), pSAI | 56 |
| BG 3007 hpr97, pSAI | 10 |
| BG 3008 scoC, pSAI | 4 |
| BG 3009 sacQ(Hy), pSAI | 5 |
| BG 3010 scoC, sacU(Hy), pSAI | 60 |
| BG 3013 sacQ(Hy), sacU(Hy), pSAI | 30 |
| BG 3015 catA, sacQ(Hy) | 26 |
| BG 3016 scoC, sacQ(Hy) | 27 |
| BG 3017 catA, sacQ(Hy), sacU(Hy), pSAI | 55 |
| BG 3020 scoC, sacQ(Hy), sacU(Hy), pSAI | 89,61 |

[1]Medium: Schaeffers nutrient broth +0.1% glucose.

I claim:

1. A Bacillus for use in the hyperproduction of an enzyme comprising:
   a) an enzyme structural gene;
   b) a functional promoter sequence selected from the group consisting of Bacillus aprE and nprE wherein the promoter is operably linked to the enzyme structural gene; and
   c) a combination of two or more mutated transcriptional regulatory genes involved in the transcriptional regulation of the promoter, wherein the combination is selected from the group consisting of a catA mutation and a sacQ(Hy) mutation, and a scoCl mutation and a sacQ(Hy) mutation.

2. A Bacillus according to claim 1 wherein the enzyme produced is subtilisin.

3. A Bacillus according to claim 1 wherein the enzyme produced is endoglycosidase H or lipase.

4. A bacillus according to claim 1 wherein the enzyme gene is fused to at least a portion of a second gene.

5. A Bacillus according to claim 1 which is constructed by introducing the enzyme structural gene, the functional promoter sequence, and the combination of two or more mutated transcriptional regulatory genes into B. subtilis I-168.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 32 base pairs
        (B) TYPE: nucleic acid
        (C) STRANDEDNESS: double
        (D) TOPOLOGY: circular (xi) SEQUENCE DESCRIPTION: SEQ ID NO:1:

GGATCCGTCG ACCTGCAGCC AAGCTTATGC AT    32

(2) INFORMATION FOR SEQ ID NO:2:

(i) SEQUENCE CHARACTERISTICS:
        (A) LENGTH: 29 base pairs
        (B) TYPE: nucleic acid
        (C) STRANDEDNESS: double
        (D) TOPOLOGY: circular (xi) SEQUENCE DESCRIPTION: SEQ ID NO:2:

GAATTCTCAT GTTTGAGCTT ATCATGCAT    29